US008907059B2

(12) United States Patent
Liu et al.

(10) Patent No.: US 8,907,059 B2
(45) Date of Patent: Dec. 9, 2014

(54) PHOSPHOPEPTIDE ENRICHMENT OF COMPOSITIONS BY FRACTIONATION ON CERAMIC HYDROXYAPATITE (75) Inventors: Ning Liu, Fremont, CA (US); Katrina Academia, Hercules, CA (US); Aran Paulus, San Jose, CA (US); Tim Wehr, Albany, CA (US); John A. Walker, II, San Leandro, CA (US); Steve Freeby, Vacaville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 406 days.

(21) Appl. No.: 12/615,080

(22) Filed: Nov. 9, 2009

(65) Prior Publication Data
US 2010/0125128 A1 May 20, 2010

Related U.S. Application Data (60) Provisional application No. 61/114,801, filed on Nov. 14, 2008.

(51) Int. Cl.
*C07K 1/14* (2006.01)
*B01J 20/04* (2006.01)
*B01D 15/38* (2006.01)
*B01J 20/282* (2006.01)
*C07K 1/16* (2006.01)

(52) U.S. Cl.
CPC ............... *B01J 20/048* (2013.01); *C07K 1/14* (2013.01); *B01D 15/3847* (2013.01); *B01J 20/282* (2013.01); *C07K 1/165* (2013.01)
USPC ........................................................ 530/344

(58) Field of Classification Search
CPC ...... C07K 1/165; C07K 1/14; B01D 15/3847; B01J 20/048; B01J 20/282
USPC ........................................................ 530/344
See application file for complete search history.

(56) References Cited

U.S. PATENT DOCUMENTS

| | | | |
|---|---|---|---|
| 5,843,731 | A | 12/1998 | Yamamoto |
| 6,406,892 | B1 | 6/2002 | Aberin et al. |
| 7,102,005 | B2 | 9/2006 | Agnew et al. |
| 7,294,614 | B2 | 11/2007 | Tchaga et al. |
| 7,300,753 | B2 | 11/2007 | Rush et al. |
| 2005/0014197 | A1 | 1/2005 | Agnew et al. |
| 2005/0209441 | A1* | 9/2005 | Lile .............................. 530/363 |
| 2006/0093640 | A1* | 5/2006 | Duneas .......................... 424/423 |
| 2006/0099604 | A1 | 5/2006 | Stevens, Jr. et al. |
| 2007/0054304 | A1 | 3/2007 | Agnew et al. |
| 2007/0227974 | A1 | 10/2007 | Anders et al. |
| 2008/0006581 | A1 | 1/2008 | Zou et al. |
| 2008/0171848 | A1 | 7/2008 | Christiansen et al. |
| 2009/0186396 | A1 | 7/2009 | Gagnon |

FOREIGN PATENT DOCUMENTS

WO WO 2009/028791 A1 3/2009

OTHER PUBLICATIONS

Delom, Frederic et al.; "Phosphoprotein analysis: from proteins to proteomes"; 2006, *Proteome Science*, vol. 4, No. 15, 12 pages.
Gagnon, Pete; "Monoclonal antibody purification with hydroxyapatite"; 2009, *New Biotechnology*, vol. 25, No. 5, pp. 287-293.
Ivanov, I. et al.; "Purification of spin-labelled DNA by hydroxyapatite chromatography"; 1983, *Journal of Chromatography*, vol. 260, pp. 177-183.
Kothari, R.M. et al.; "RNA Fractionation on Hydroxyapatite Columns"; 1974, *Journal of Chromatography*, vol. 98, pp. 449-475.
Li, Yan et al.; "Highly selective and rapid enrichment of phosphorylated peptides using gallium oxide-coated magnetic microspheres for MALDI-TOF-MS and nano-LC-ESI-MS/MS/MS analysis"; 2008, *Proteomics*, vol. 8, pp. 238-249.
Machida, Mitsuyo et al.; "Purification of phosphoproteins by immobilized metal affinity chromatography and its application to phosphoproteome analysis"; 2007, *FEBS Journal*, vol. 274, pp. 1576-1587.
Mazanek, Michael et al.; "Titanium dioxide as a chemo-affinity solid phase in offline phosphopeptide chromatography prior to HPLC-MS/MS analysis"; 2007, *Nature Protocols*, vol. 2, No. 5, pp. 1059-1069.
Paradela, Alberto et al.; "Advances in the Analysis of Protein Phosphorylation"; 2008, *Journal of Proteome Research*, vol. 7, pp. 1809-1818.
Schilling, Michael et al.; "Enrichment of Phosphopeptides Using Biphasic Immobilized Metal Affinity-Reversed Phase Microcolumns"; 2008, *Journal of Proteome Research*, vol. 7, pp. 4164-4172.
Reinders, Joerg et al.; "State-of-the-art in phosphoproteomics"; 2005, *Proteomics*, vol. 5, pp. 4052-4061.
Thingholm, Tine E. et al.; Highly selective enrichment of phosphorylated peptides using titanium dioxide; 2006, *Nature Protocols*, vol. 1, No. 4, pp. 1929-1935.
Zhou, Houjiang et al.; "Highly specific enrichment of phosphopeptides by zirconium dioxide nanoparticles for phosphoproteome analysis"; 2007, *Electrophoresis*, vol. 28, pp. 2201-2215.
Schmidt, et al., "Current Methods for Phosphoprotein Isolation and Enrichment," J Chromatography B., Oct. 10, 2006, 849:154-162, pp. 155-162.
Gagnon, "An Enigma Unmasked: How Hydroxyapatite Works, and How to Make it Work for You," Validated Biosystems Quarterly Resource Guide for Downstream Processing, 1998, retrieved from the internet Mar. 18, 2010 http://www.validated.com/revalbio/pdfiles/hxyapt.pdf, pp. 1-9.

(Continued)

*Primary Examiner* — Julie Ha
(74) *Attorney, Agent, or Firm* — Kilpatrick Townsend & Stockton LLP (57) ABSTRACT Phosphorylated peptides are extracted from digests of biological liquids and other peptide mixtures by fractionation on ceramic hydroxyapatite. The ceramic hydroxyapatite is readily usable in a centrifuge, allowing for rapid fractionations of a large number of small volume samples, and accordingly high throughput.

11 Claims, 7 Drawing Sheets

(56) References Cited

OTHER PUBLICATIONS

Gagnon, et al., "A Ceramic Hydroxyapatite-Based Purification Platform Simultaneous Removal of Leached Protein A, Aggregates, DNA, and Endotoxins from MAbs," BioProcess International, Feb. 2006, retrieved from the internet May 18, 2010 http://www.validated.com/revalbio/pdfiles/bpicht.pdf, pp. 50-60.

Nordstrom, et al., "Generation of a New Protein Purification Matrix by Loading Ceramic Hydroxyapatite with Metal Ions—Demonstration with Poly-Histidine Tagged Green Fluorescent Protein," J Biotechnology, 1999, vol. 69, pp. 25-133.

Liu, et al., "Ceramic Hydroxyapatite-Based Phosphoprotein/Peptide Enrichment Facilitates Biochemical Study of Tau," Alzheimer's and Dementia, Jul. 2009, 5 (Poster Presentations P4-197), pp. 488-489.

Wikiel, et al., "Hydroxyapatite Mineralization and Demineralization in the Presence of Synthetic Phosphorylated Pentapeptides," *Archs oral Biol.*, vol. 39(8), pp. 715-721 (1994).

Yin, et al., "Multi-component adsorption model for pellicle formation: The influence of salivary proteins and non-salivary phospho proteins on the binding of histatin 5 onto hydroxyapatite," *Archives of Oral Biology*, vol. 51, pp. 102-110 (2006).

Ogawa et al.; "Effect of pH on gradient elution of different proteins on two types of ceramic hydroxyapatite"; *International Laboratory*; 27(1):11-13 (1997).

Lori, et al., "Mechanism for the Adsorption of Mucin on Hydroxyapatite," *Nigerian Journal of Chemical Research*, vol. 10, pp. 21-29 (2005).

\* cited by examiner

PHOSPHOPEPTIDE ENRICHMENT OF COMPOSITIONS BY FRACTIONATION ON CERAMIC HYDROXYAPATITE

CROSS REFERENCE TO RELATED APPLICATION

This application claims the benefit of U.S. Provisional Patent Application No. 61/114,801, filed Nov. 14, 2008, the contents of which are incorporated herein by reference.

BACKGROUND OF THE INVENTION

1. Field of the Invention

This invention lies in the fields of phosphorylated peptides and the fractionation of peptides in general.

2. Background of the Invention

Analyses of phosphorylated peptides are used in studies of protein functions and biological systems. Protein phosphorylation occurs during posttranslational modification of proteins and in many cases is crucial to the preservation and regulation of protein structure and function. Enzymatically catalyzed phosphorylation and dephosphorylation are important regulatory functions of living cells, contributing to cell proliferation, development, and differentiation, signal transduction, nerve activity, organization of the cytoskeleton, programmed cell death, and gene expression. The determination of phosphorylation sites, performed by digestion of proteins and analysis of the resulting peptides, is thus an important factor in understanding complex biological systems and the development of diseases. Studies of phosphorylated proteins and peptides are made difficult however by the relatively small amounts of these species in biological fluids. Various methods have therefore been developed to achieve selective enrichment of phosphorylated species.

One widely reported means of enrichment of phosphorylated proteins and peptides is immobilized metal chelate affinity chromatography (IMAC). This technique uses separation media that have been surface-modified by the addition of metal ions through chelating agents, and the isolation of phosphopeptides occurs as the result of a strong interaction between the immobilized metal ions and the phosphate groups on the peptides. Various amino acids, however, also display an interaction with the metal ions by acting as electron donors. This competes with the phosphorylated species, and limits the selectivity of the separation. Another difficulty with IMAC is that elution of the bound phosphopeptides is not quantitative, and this limits the efficiency of the separation. High yield and high purity for phosphopeptide enrichment thus remain elusive.

Of further potential relevance to the background of this invention are disclosures of the use of ceramic hydroxypatite (CHT) as a chromatographic separation medium. Disclosures of the use of CHT to purify monoclonal antibodies appear in the review article of Gagnon, P., "Monoclonal antibody purification with hydroxyapatite," New Biotechnol. 25(5): 287-293 (2009); disclosures of CHT to isolate DNA are reported by Ivanov, I., et al., "Purification of spin-labeled DNA by hydroxyapatite chromatography," J. Chromatog. 260: 177-183 (1983); and disclosures of CHT to isolate RNA are reported by Kothari, R. M., et al., "RNA Fractionation on hydroxyapatite columns," J. Chromatog. 98(2): 449-475 (1974). A disclosure of phosphorylated proteins from their non-phosphorylated forms on CHT appears in Schmidt, S. R., et al., "Current methods for phosphoprotein isolation and enrichment," J. Chromatog. B 849: 154-162 (2006).

SUMMARY OF THE INVENTION

It has now been discovered that phosphorylated peptides (also referred to herein as "phosphopeptides") can be selectively extracted to a high yield and purity from mixtures of proteins, peptides, or both, that include both phosphorylated and non-phosphorylated species, and that such mixtures can be enriched in phosphorylated peptides, by chromatographic fractionation of the mixtures over ceramic hydroxyapatite. This success in achieving phosphopeptide enrichment with CHT is not within naturally expectations from the disclosures of phosphoprotein enrichment with CHT in view of the fundamental differences between peptides and proteins. Included among these differences are differences in molecular size and the fact that peptides tend not to assume the three-dimensional structures that are characteristic of proteins, including such structures as beta-sheets and alpha-helical conformations of typical proteins. Starting mixtures that contain phosphopeptides together with non-phosphorylated species, including such mixtures where the non-phosphorylated species are present in high concentrations can be effectively enriched in phosphopeptides by this method, and enrichments at high throughput are readily achievable with conventional chromatographic equipment, and particularly with spin columns or centrifuges. Phosphopeptide enrichment in this invention means treatment of a starting solution containing the phosphopeptide(s) and non-phosphorylated peptides (and possibly non-phosphorylated proteins as well) to achieve a treated solution that has a higher proportion of the phosphopeptide(s) relative to the other peptides (and proteins) than the starting solution. In general terms, a solution that is enriched in phosphopeptides relative to another solution means that the former contains a higher proportion of phosphopeptides relative to the non-phosphorylated peptides (and proteins) than the latter.

The present invention offers several advantages. First, in addition to producing a solution enriched in phosphopeptides from mixtures that contain the phosphopeptides together with non-phosphorylated peptides and in some cases phosphoproteins as well, the invention allows the separation of mono-phosphorylated species from multi-phosphorylated species (i.e., proteins or peptides containing two or more phosphoryl groups per molecule). Second, the extractions can be performed in short periods of time on samples of small volume, which allows for high throughput enrichments by processing multitudes of small samples simultaneously, particularly in spin columns or centrifuges. Third, ceramic hydroxyapatite sustains high pressure, which makes it suitable for use in a centrifuge operating at high speed. Fourth, ceramic hydroxyapatite is a self-supporting resin that does not require a support such as agarose or methacrylate polymers. This lack of an additional support lowers the possibility of non-specific protein or peptide binding.

DETAILED DESCRIPTION OF THE INVENTION AND PREFERRED EMBODIMENTS

The term "peptide" is used herein to denote an oligomer of amino acids, typically containing a maximum of thirty amino acids. The mass-to-charge ratios (M/Z) of the peptides to which this invention is preferably directed in certain embodiments are within the range of from about 500 to about 5000, in certain other embodiments from about 500 to about 3000, and in certain other embodiments form about 1000 to about 3000. The terms "phosphopeptide" and "phosphorylated peptide" are used interchangeably to denote peptides that bear at least one phosphoryl group chemically bonded to the amino acid chain that forms the backbone of the molecule. The phosphopeptides in which compositions can be enriched by this invention include peptides to which a single phosphoryl group is bonded as well as peptides to which two or more phosphoryl groups are bonded. As will be explained further below and illustrated, phosphopeptides of different degrees of phosphorylation (i.e., having different numbers of bound phosphoryl groups per molecule) can be separated from each other on the basis of their degrees of phosphorylation by the process of the present invention.

Ceramic hydroxyapatite (CHT) is a chemically pure form of hydroxyapatite that has been sintered at high temperatures. It is spherical in shape, with particle sizes ranging from about 10 microns to about 100 microns in diameter, and is typically available at nominal diameters of 20 microns, 40 microns, and 80 microns. Ceramic hydroxyapatite is macroporous, and is available from Bio-Rad Laboratories, Inc. (Hercules, Calif., USA), in two types: Type I, with a relatively high porosity and correspondingly high binding capacity, and Type II, with a lower porosity and binding capacity. Either porosity can be used, and the optimal porosity for any particular phosphopeptide enrichment procedure will vary with the composition of the mixture prior to enrichment and the source of the mixture. The ceramic hydroxyapatite is preferably used by itself, rather than in admixture with any other separation medium or support, and not functionalized beyond its naturally occurring chemical composition.

In preferred embodiments of the invention, the CHT itself is enriched in calcium ions prior to use. This can be achieved by incubation of the CHT with a solution of a calcium salt, preferred examples of which are calcium halides, and notably calcium chloride. An aqueous solution of the calcium salt at a concentration within the range of about 30 mM to about 300 mM for example can serve as an effective treatment medium. The solution is preferably maintained at approximately a neutral pH by the inclusion of an appropriate buffer, as known among those skilled in the art.

The enrichment process can be performed by any conventional chromatographic procedure which involves contact between a sample of the liquid solution to be enriched and a solid-phase separatory medium. The separatory medium, in this case CHT, can thus be a fixed bed or a fluidized bed, and if a fixed bed, any form of CHT that will allow high-surface contact between the CHT and the liquid phase and flow-through of the liquid phase, such as a packed bed of beads, granules, or particles or a frit or otherwise consolidated foraminous mass. Fixed beds are preferred, and CHT beads are particularly preferred due to their availability from commercial suppliers. The sample is typically applied to the solid phase with a binding buffer. The binding buffer is preferably alkaline, and a preferred pH range in certain embodiments is from about 8 to about 10, in certain other embodiments from about 8.5 to about 9.5, and in certain other embodiments from about 8.0 to about 9.0. An example of a suitable alkaline binding buffer is a solution of acetonitrile and sodium bicarbonate, preferably such a solution at a pH of about 8.5.

Alkaline elution buffers are also used in preferred embodiments. In certain embodiments, an elution buffer that is at the same pH as the binding buffer is used, while in certain other embodiments, an elution buffer at a higher pH is used, or a succession of elution buffers at successively higher pH. A single elution buffer can be used, in which case a high-stringency buffer, i.e., one that has a high ionic strength and a high pH, is preferred. An example of such a buffer is one containing potassium phosphate monobasic at a concentration of from about 0.3M to about 3M, preferably from about 0.5M to about 2M, and a pH of about 9.0 to about 11.0, preferably from about 9.5 to about 10.5. When two or more elution buffers of successively higher pH are used, the first will be a low-stringency buffer and the second a high-stringency buffer. In certain embodiments, the low-stringency buffer has a higher salt concentration than the high-stringency buffer, and the higher salt concentration can be achieved by including an additional salt in the low-stringency buffer that is not included in the high-stringency buffer, or by using the same salt or salt combinations in both but at different concentrations. Differences in salt concentrations can also be achieved by using salts with different dissociation constants. For example, when both the low-stringency and high-stringency buffers contain a salt of limited dissociation such as sodium phosphate monobasic, the low-stringency buffer can also include a highly dissociable salt such as sodium chloride in addition to the sodium phosphate or to replace a portion of the sodium phosphate. In other embodiments, the low-stringency buffer is one with a relatively low ionic strength and a pH that is intermediate in value between the pH of the binding buffer and the pH of the high-stringency elution buffer. In these embodiments, the low-stringency buffer preferably has a pH of about 8.5 to about 9.5 and the high-stringency buffer has a pH that exceeds the pH of the low-stringency buffer by a differential of 0.5 to 2.0, and preferably a differential of 0.75 to 1.5. A particularly preferred low-stringency alkaline buffer suitable is one containing acetonitrile, tris-(hydroxymethyl)-aminomethane, and sodium phosphate monobasic at a pH of about 8.5 to about 9.5, preferably about 9.0, and a particularly preferred a high-stringency buffer is one containing potassium phosphate monobasic at a pH of about 9.5 to about 10.5, preferably about 10.0.

The following examples are offered for purposes of illustration only.

EXAMPLE 1

Ceramic hydroxyapatite Type I, 20 microns in particle size, was used with the following buffer solutions in which all percents are by weight:

| | |
|---|---|
| Binding Buffer | 40 mM Tris, pH 9 |
| | 25 mM NaH$_2$PO$_4$ |
| | (no Urea, Thiourea, or CHAPS) |
| Low Stringency Elution Buffer | 40 mM Tris, pH 9 |
| | 25 mM NaH$_2$PO$_4$ |
| | 500 mM NaCl |
| | (no Urea, Thiourea, or CHAPS) |
| High Stringency Elution Buffer | 500 mM NaH$_2$PO$_4$, pH 7.5 |
| | (no Urea, Thiourea, or CHAPS) |

*CHAPS: 3-[(3-cholamidopropyl)dimethylammonio]-1-propanesulfonic acid

Micro Bio-Spin columns of Bio-Rad Laboratories, Inc. (Catalog No. 732-6204) were packed with 40 mg to 200 mg of Ceramic Hydroxyapatite (CHT) Type I, 20 micron diameter beads (Bio-Rad Laboratories, Inc.) over a ten-micron frit. Binding buffer (500 μL) was added to each column, and the buffer and meads were mixed and incubated in the column for two minutes. The columns were then spun at 5,000×g for thirty seconds, and the flow-through buffer was discarded. The sample was then prepared in the binding buffer, and a quantity (0.5-1.0 mL) was added to each column where it was mixed and incubated with the CHT beads for five minutes at room temperature (20-25° C.). The columns were then spun at 5,000×g for thirty seconds, and the flow-through fraction was collected. Further binding buffer (500 μL) was then added to each column as a first wash solution, followed by spinning of the columns at 5,000×g for thirty seconds. Second and third wash solutions, identical to the first, were then added, followed by spinning at the same rate and duration. All three wash fractions were collected and the wash fractions were pooled with the flow-through fraction for analysis. Three 500-μL aliquots of the low-stringency buffer were then added successively to each column, each aliquot followed by spinning of the columns at 5,000×g for thirty seconds and collection of the eluate. Three 500-μL aliquots of the high-stringency buffer were then added to each column, each aliquot followed by spinning of the columns at 5,000×g for thirty seconds and collection of the eluate. The low-stringency and high-stringency eluates were separately pooled.

Figure 1:
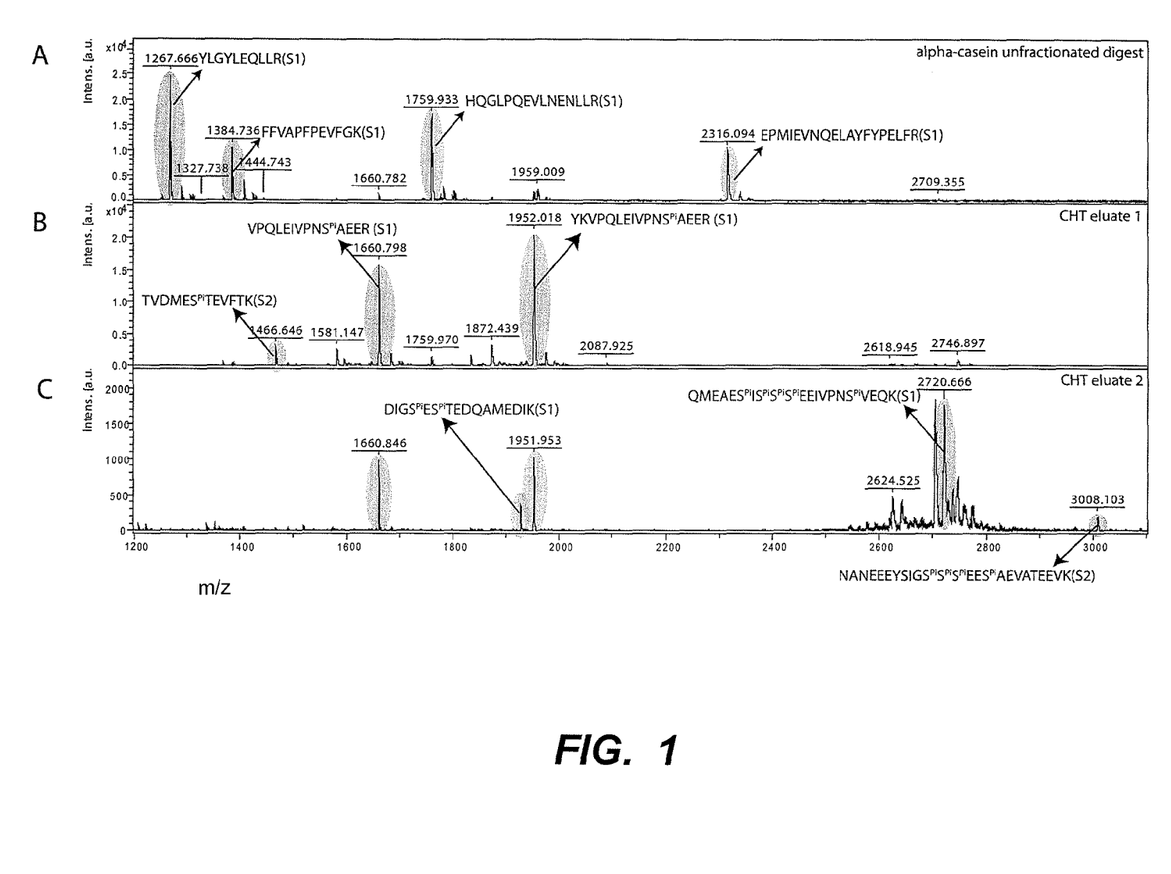
FIGS. 1A, 1B, and 1C are MALDI spectra of the flow-through fraction, low-stringency eluate, and high-stringency eluate, respectively, of a trypsin digest of alpha-casein fractionated according to the present invention.

The sample that was fractionated was a mixture of peptides resulting from the trypsin digestion of α-casein. The unfractionated digest, pooled low-stringency eluates, and pooled high-stringency eluates were analyzed by matrix-assisted laser desorption ionization (MALDI), and the results are shown in FIG. 1 in Spectra A, B, and C, respectively. In the unfractionated digest spectrum (Spectrum A), the dominant peaks are indicated by arrows pointing to the peptide sequences, and all represent non-phosphorylated peptides. In the low-stringency eluate spectrum (Spectrum B), the dominant peaks likewise are indicated by arrows pointing to the peptide sequences, and all are phosphopeptides that were undetectable in the unfractionated digest spectrum. In the high-stringency eluate spectrum (Spectrum C), the dominant peaks likewise are indicated by arrows pointing to the peptide sequences, and all are phosphopeptides that were undetectable in the unfractionated digest spectrum. The phosphopeptides in the low-stringency eluate pool were mostly singly phosphorylated, while those in the high-stringency eluate pool were mostly multiply phosphorylated.

Examples 2 through 6 illustrate the use of CHT for the extraction of phosphorylated peptides from several mixtures of phosphorylated peptides and non-phosphyorylated peptides, including both mixtures that are commercially available standards and mixtures that were prepared by digestion of phosphorylated proteins with trypsin. For those mixtures prepared by digestion, the starting protein was reconstituted in 100 μL 6M urea and 50 mM Tris at pH 8.0, and 200 mM dithiothreitol/50 mM Tris-HCl, pH 8.0 was added, and the resulting mixture incubated for 1 h at room temperature. A 20-μL quantity of 200 mM iodoacetamide/50 mM tris-HCl, pH 8.0, was then added and the mixture vortexed and incubated for 1 h at room temperature in the dark. This was followed by the addition of 20 μL of 200 mM dithiothreitol/50 mM Tris-HCL at pH 8.0 and incubating for 1 h at room temperature in the dark, and then the addition of 775 μL of water to reduce the urea concentration to 0.6M. Trypsin solution was then added to a final ratio of 1:50 (by weight) trypsin: protein, followed by vortexing and incubating at 37° C. for 16-20 h. Digests prepared in this manner were stored at −20° C.

For all extractions, the ceramic hydroxyapatite (CHT) resin of the same type and source as that used in Example 1 was used, except that prior to use the resin was calcium-enhanced by placing 200 mg of CHT resin and 1 mL of a 100 mM calcium chloride solution (buffered with 50 mM 2-(N-morpholino)ethanesulfonic acid (Mes) at pH 7.0) in a microcentrifuge tube and vortexing the mixture for ten seconds, then spinning at 13,000 g for thirty seconds, and vortexing and spinning again twice. The calcium-treated resin was then stored in the calcium chloride solution. A 10-mg quantity of the calcium-treated resin was then spun in a microcentrifuge tube and the liquid discarded.

The fractionation procedure used in Examples 2 through 6 was as follows. A 500-mL quantity of a binding buffer whose concentration is specified in each example was added to the resin and spun and the wash discarded, followed by two more 500-mL quantities of the binding buffer, each time with spinning and discarding of the wash. A further 200 μL of the binding buffer and 1-10 μL of the peptide mixture were then added and the contents vortexed and spun for ten minutes at room temperature. The supernatant was then recovered. The resin was then washed three times with 500 mL each of the binding buffer, and the supernatant recovered each time. The supernatants were pooled to constitute the flow-through fraction. Elution was then performed in two stages. For the first stage, a 100-μL quantity of a low-stringency elution buffer whose concentration is specified in each example was added, followed by vortexing and spinning. The supernatant was then removed, a further 100-μL quantity of the low-stringency elution buffer added, vortexed, and spun, and the supernatant pooled with the first supernatant as the low-stringency eluate. For the second stage, a 100-μL quantity of a high-stringency elution buffer whose concentration is specified in each example was added to the resin, followed by vortexing and spinning. The supernatant was then removed, a further 100-μL quantity of the high-stringency elution buffer added, the resulting mixture vortexed and spun, and the supernatant pooled with the first supernatant as a high-stringency eluate. The pooled flow-through fraction and the two pooled eluates were then concentrated by evaporation, and all three were adjusted to pH 3.0 with 10% trifluoroacetic acid.

The pooled flow-through fraction and the pooled low-stringency and high-stringency eluates were then concentrated further to volumes of 3-5 μL and transferred to a Bruker MTP Anchor Chip (Broker Daltonics, Billerica, Mass., USA), where they were treated with an acetonitrile solution of 2,5-dihydroxybenzoic acid and analyzed by matrix-assisted laser desorption/ionization time-of-flight (MALDI-TOF) mass spectroscopy.

EXAMPLE 2

Figure 2:
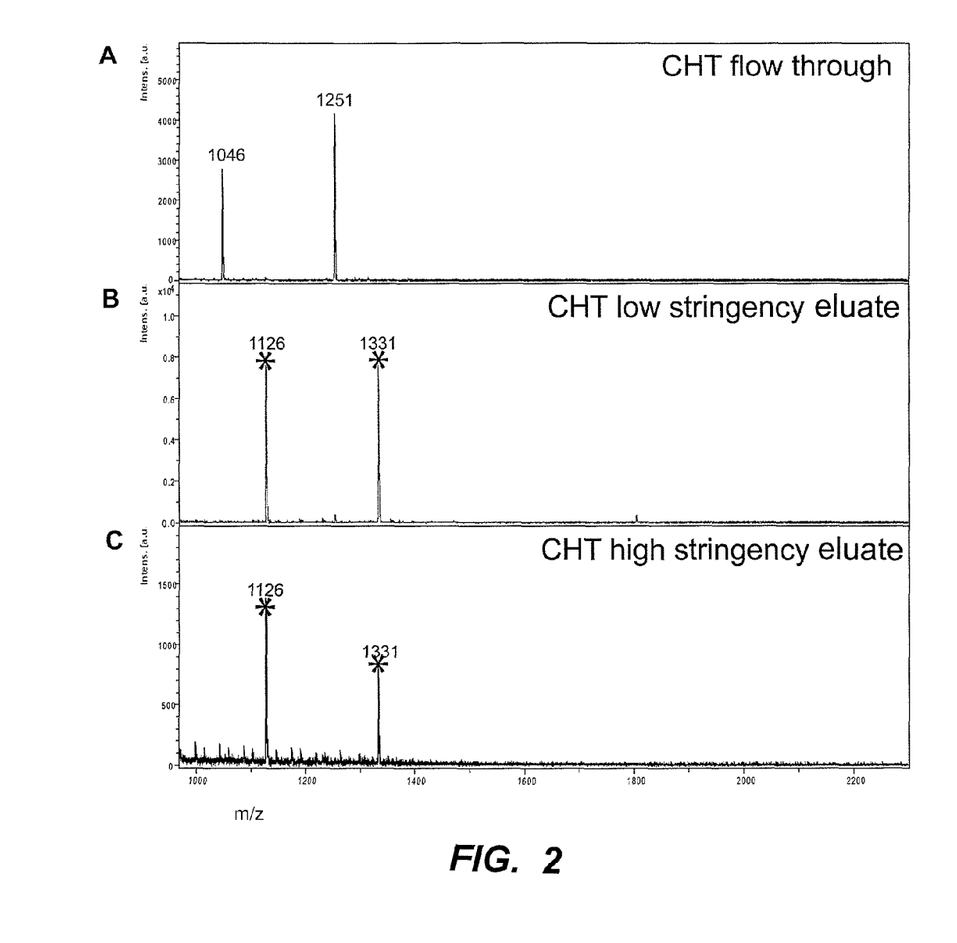
FIGS. 2A, 2B, and 2C are MALDI spectra of the flow-through fraction, low-stringency eluate, and high-stringency eluate, respectively, of a Protea standard peptide mixture fractionated according to the present invention.

The sample used in this example was a Protea peptide standard PS-181 (Protea Biosciences, Inc., Morgantown, W.V., USA). This standard consisted of three peptides (M/Z 1046, 1251, 1722) and their singly-phosphorylated forms (M/Z 1125(pY), 1331(pS), 1802(pT)). The mixture was applied to the CHT beads using 50% acetonitrile and 0.5 mM Tris as the binding buffer. Elution was then performed, using a buffer containing 1 mM Tris and 25 mM methylphosphonate, pH 8.5 as the low-stringency buffer and a buffer containing 500 mM sodium phosphate, pH 9.0 as the high-stringency buffer. The results are shown in FIG. 2 of which Part A is the spectrum of the flow-through fraction, Part B is the spectrum of the low-stringency eluate, and Part C is the spectrum of the high-stringency eluate. The spectra show that the non-phosphorylated peptides 1046 and 1251 were in the flow-through fraction, and the phosphopeptides 1126(pY) and 1331(pS) were in both eluates. This indicates a clear separation of two phosphopeptides from their non-phosphorylated forms.

EXAMPLE 3

Figure 3:
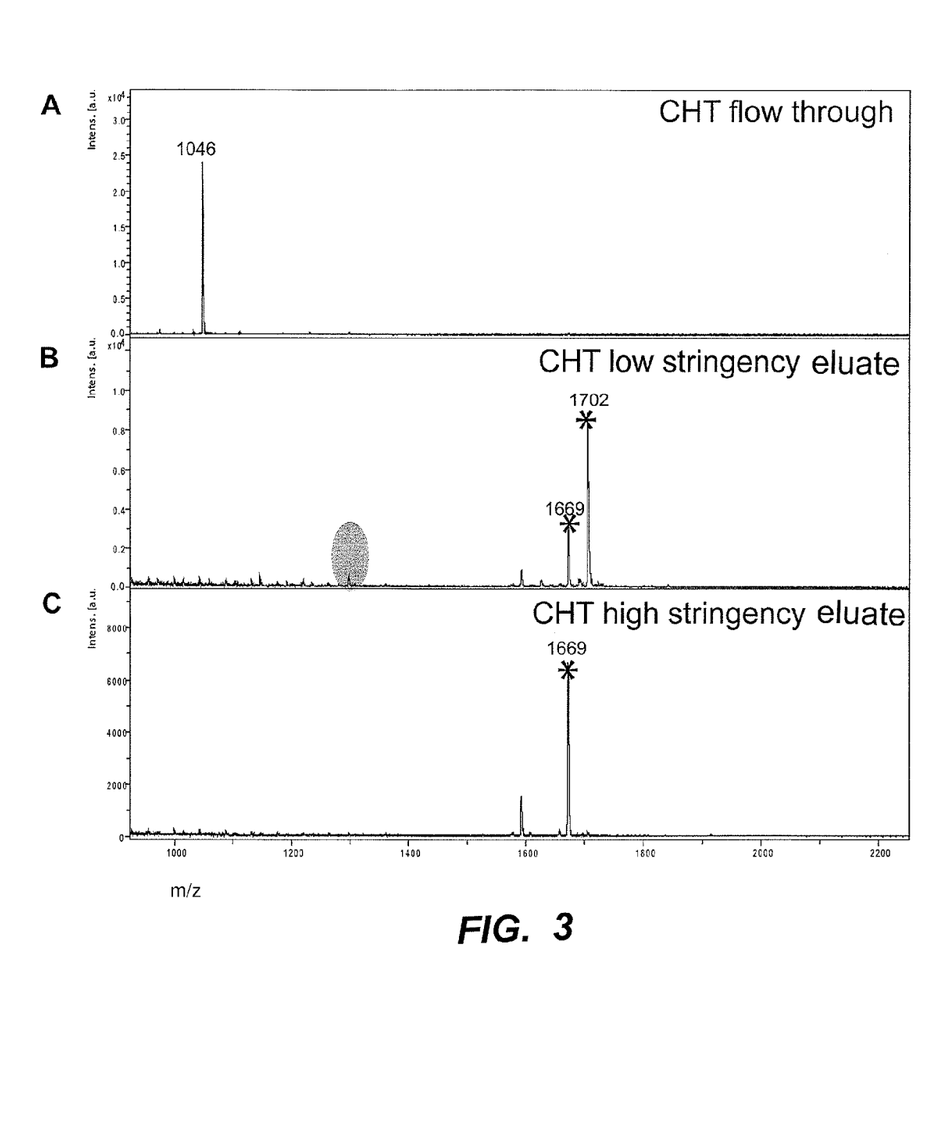
FIGS. 3A, 3B, and 3C are MALDI spectra of the flow-through fraction, low-stringency eluate, and high-stringency eluate, respectively, of an Invitrogen standard peptide mixture fractionated according to the present invention.

The sample used in this example was an Invitrogen peptide standard P33357 (Invitrogen Corporation, Carlsbad, Calif., USA) consisting of three peptides (M/Z 1046, 1296, 1578) and four phosphopeptides with phosphorylation on different amino acid residues (M//Z 1669(pTpY), 1702(pY), 1720(pT), and 2192(pS)). The mixture was applied to the CHT beads using 50% acetonitrile and 0.5 mM Tris as the binding buffer. Elution was then performed, using a buffer containing 1 mM Tris and 25 mM methylphosphonate, pH 8.5 as the low-stringency buffer and a buffer containing 500 mM sodium phosphate, pH 9.0 as the high-stringency buffer. The results are shown in FIG. 3 of which Part A is the spectrum of the flow-through fraction, Part B is the spectrum of the low-stringency eluate, and Part C is the spectrum of the high-stringency eluate. The spectra show that the non-phosphorylated peptide 1046 was detected only in the flow-through fraction and the phosphopeptides 1669(pTpY) and 1702(pY) were detected in both eluates and not in the flow-through fraction. The non-phosphorylated peptide 1297 was detected in both the flow-through fraction and the low-stringency eluate. Two of the phosphopeptides were thus separated from the mixture by the fractionation.

EXAMPLE 4

The sample used in this example was a phosphorylated α-casein digest (using a highly phosphorylated α-casein from Sigma-Aldrich, St. Louis, Mo., USA). The digest was applied to the CHT beads using a buffer containing 20% acetonitrile, 25 mM sodium bicarbonate, and 500 mM NaCl, pH 8.5, as the binding buffer, and elution was performed using a mixture of 10% acetonitrile, 40 mM Tris, and 25 mM $NaH_2PO_4$, pH 9.0, as the low-stringency elution buffer and 1 mM $KH_2PO_4$, pH 10.0, as the high-stringency elution buffer.

Figure 4:
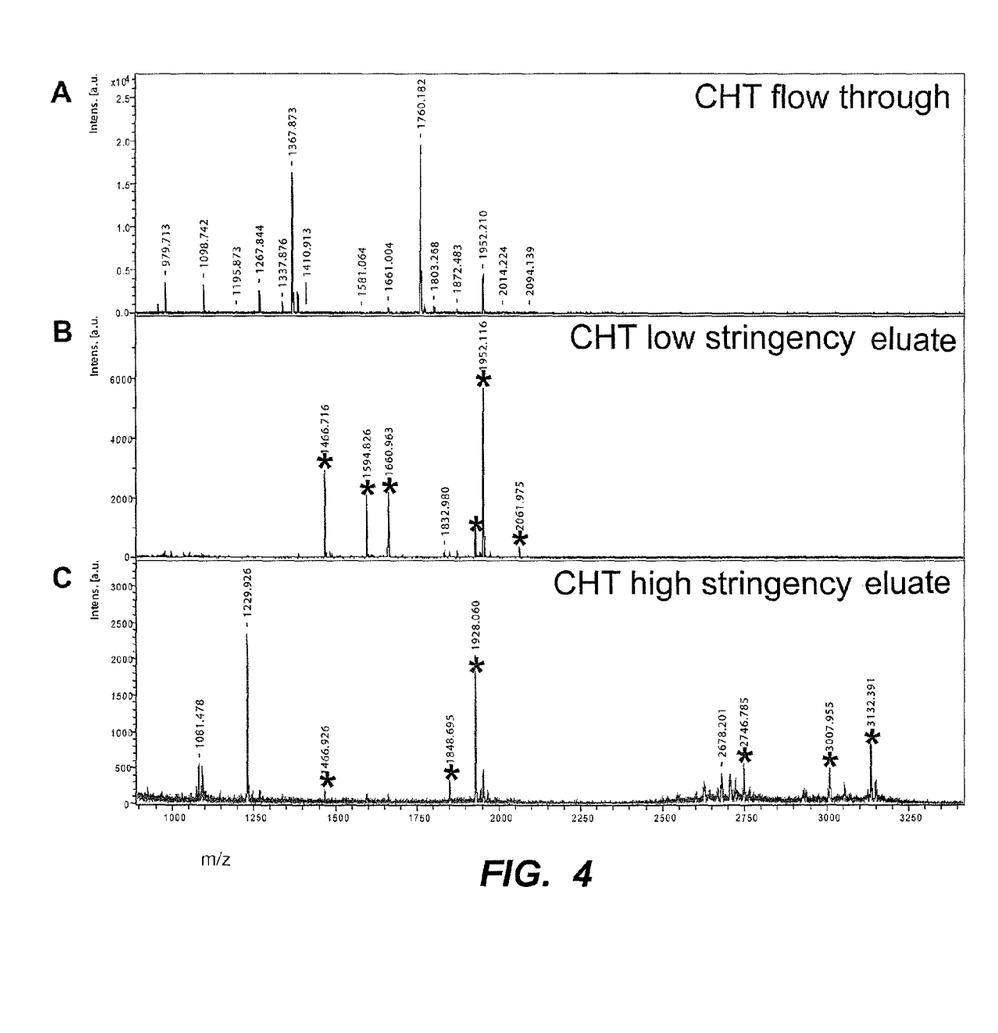
FIGS. 4A, 4B, and 4C are MALDI spectra of the flow-through fraction, low-stringency eluate, and high-stringency eluate, respectively, of a trypsin digest of alpha-casein fractionated according to the present invention under conditions other than those of FIGS. 1A, 1B, and 1C.

The results are shown in FIG. 4 of which Part A is the spectrum of the flow-through fraction, Part B is the spectrum of the low-stringency eluate, and Part C is the spectrum of the high-stringency eluate. The spectra indicate that the dominant peaks in the flow-through fraction were non-phosphorylated α-casein peptides. The dominant peaks in the low-stringency eluate were mostly singly-phosphorylated peptides, and the dominant peaks in the high-stringency eluate were mostly multiply-phosphorylated peptides. Separation of the phosphorylated from the non-phosphorylated peptides was thus demonstrated in this experiment as well.

EXAMPLE 5

Comparative

The sample used in this example was a bovine serum albumin digest, using bovine serum albumin from Sigma-Aldrich, St. Louis, Mo., USA. This protein is a non-phosphorylated protein included herein for comparison with digests containing phosphopeptides. The BSA was digested in trypsin as described above, and the digest was applied to the CHT beads using a buffer containing 20% acetonitrile, 25 mM sodium bicarbonate, and 500 mM NaCl, pH 8.5, as the binding buffer, and elution was performed using a mixture of 10% acetonitrile, 40 mM Tris, and 25 mM $NaH_2PO_4$, pH 9.0, as the low-stringency elution buffer and 1 mM $KH_2PO_4$, pH 10.0, as the high-stringency elution buffer, as in Example 4.

Figure 5:
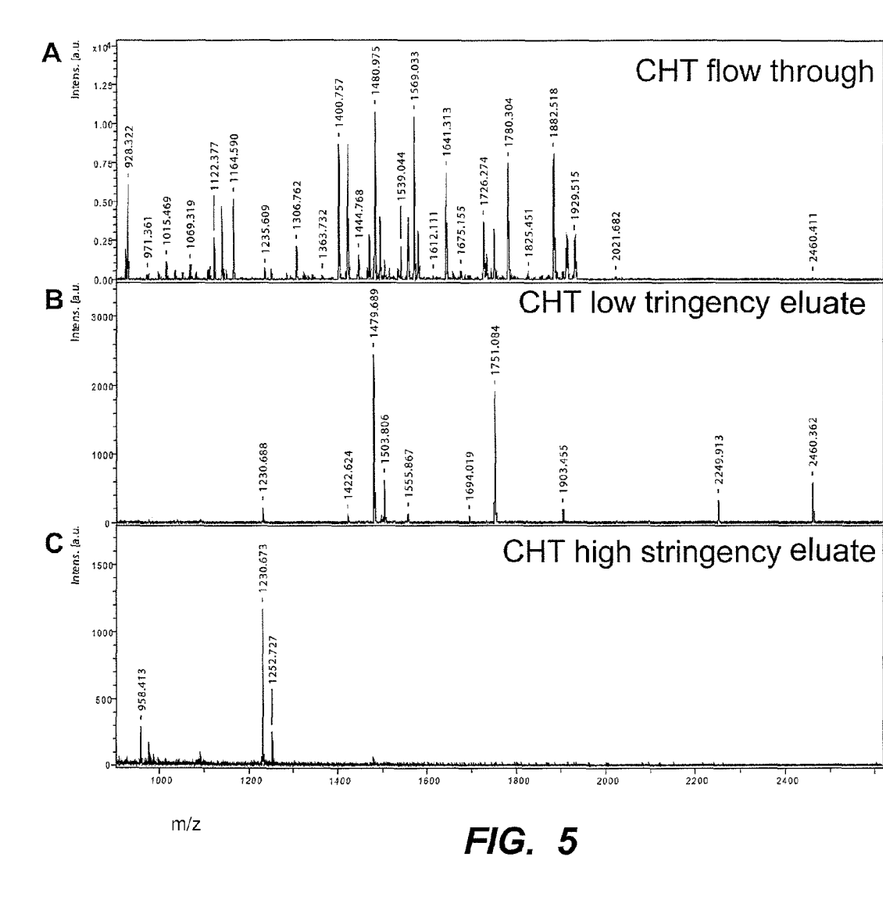
FIGS. 5A, 5B, and 5C are MALDI spectra of the flow-through fraction, low-stringency eluate, and high-stringency eluate, respectively, of a comparative tests outside the scope of this invention, utilizing a peptide mixture (a trypsin digest of bovine serum albumin) containing non-phosphorylated peptides only.

The results are shown in FIG. 5 of which Part A is the spectrum of the flow-through fraction, Part B is the spectrum of the low-stringency eluate, and Part C is the spectrum of the high-stringency eluate. The spectra show that while a small proportion of the peptides were detected in the low-stringency eluate, most of the peptides were detected in the flow-through fraction, and none were detected in the high-stringency eluate. The five to seven peptides detected in the low-stringency eluate were passed through the column again, but this failed to remove the peptides from the eluant, which indicated that these peptides did not bind strongly to the CHT.

EXAMPLE 6

The samples used in this example were mixtures of a α-casein digest and a BSA digest. These samples were run to determine whether CHT will enrich phosphopeptides from a complex sample in which the phosphopeptides are present in low amounts relative to the peptides as a whole. Mixtures of the two digests with weight ratios of 1:10 and 1:90 (casein:BSA) were used. Each digest was applied to the CHT beads using a buffer containing 20% acetonitrile, 25 mM sodium bicarbonate, and 500 mM NaCl, pH 8.5, as the binding buffer, and elutions were performed using a mixture of 10% acetonitrile, 40 mM Tris, and 25 mM $NaH_2PO_4$, pH 9.0, as the low-stringency elution buffer and 1 mM $KH_2PO_4$, pH 10.0, as the high-stringency elution buffer.

Figure 6:
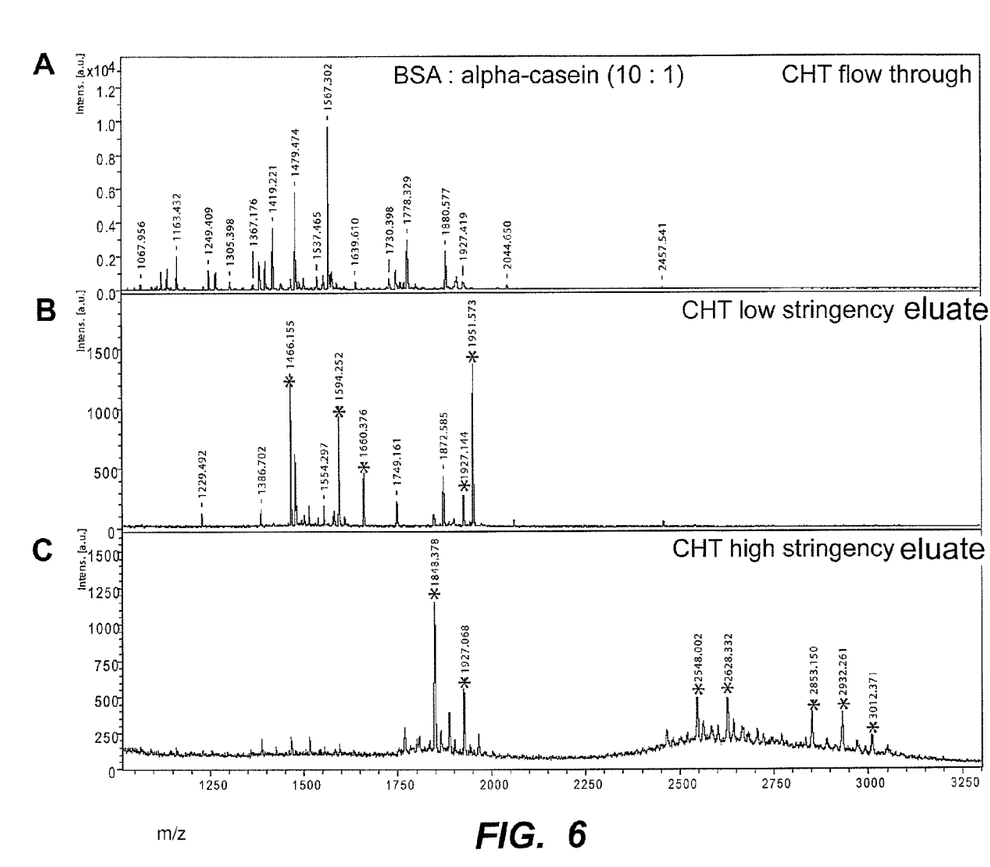
FIGS. 6A, 6B, and 6C are MALDI spectra of the flow-through fraction, low-stringency eluate, and high-stringency eluate, respectively, of a peptide mixture prepared by combining trypsin digests of alpha-casein and BSA, fractionated according to the present invention.
Figure 7:
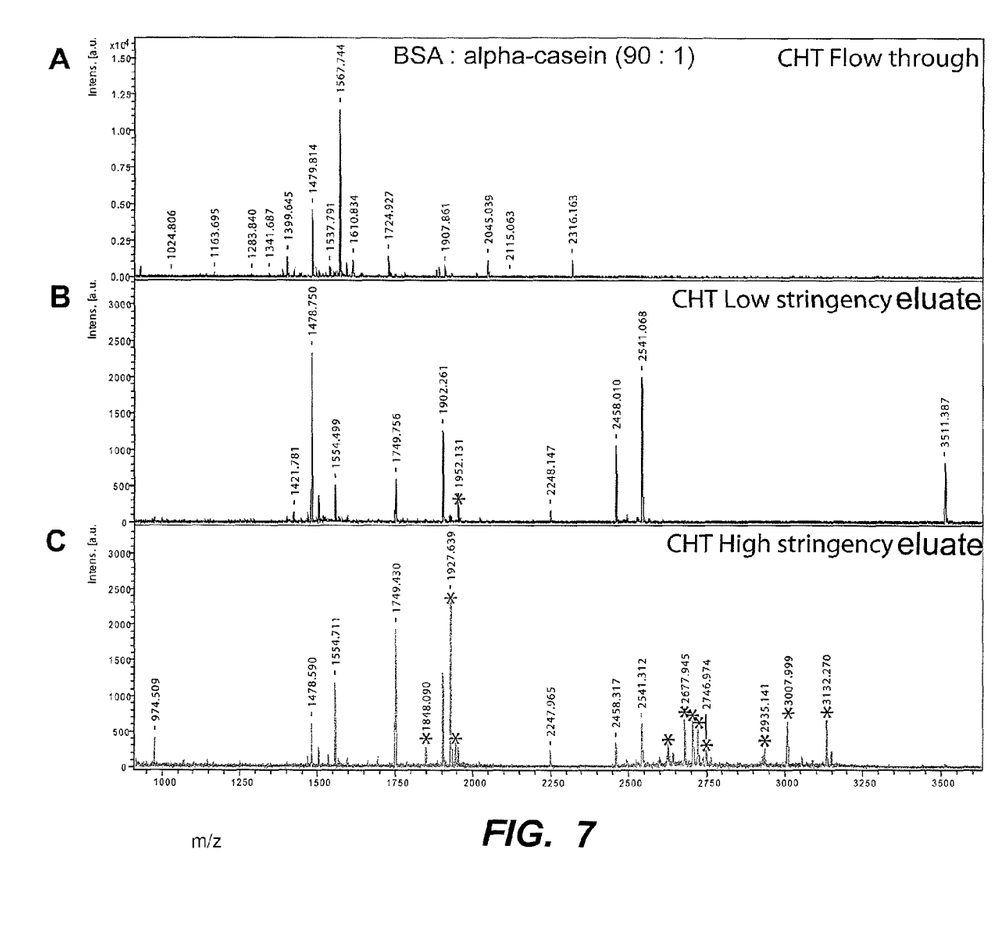
FIGS. 7A, 7B, and 7C are MALDI spectra of the flow-through fraction, low-stringency eluate, and high-stringency eluate, respectively, of a peptide mixture prepared by combining trypsin digests of alpha-casein and BSA at a different proportion that that of FIGS. 6A, 6B, and 6C, fractionated according to the present invention.

The results are shown in FIGS. 6 and 7, Part A of each Figure being the spectrum of the flow-through fraction, Part B being the spectrum of the low-stringency eluate, and Part C being the spectrum of the high-stringency eluate. In the 1:10 experiment (FIG. 6), the peptides detected in the low-stringency eluate were mostly α-casein peptides with single phosphoryl groups, while the α-casein peptides with multiple phosphoryl groups were detected in the high-stringency eluate. A few BSA peptides (non-phosphorylated) were detected in the eluates but only as minor peaks. In the 1:90 experiment (FIG. 7), the peptides in the low-stringency eluate were mainly BSA peptides with only one α-casein peptide, while the peptides in the high-stringency eluate were α-casein peptides with multiple phosphoryl groups in addition to a small number of BSA peptides.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for fractionating a mixture comprising phosphorylated and non-phosphorylated peptides to produce a product solution enriched in said phosphorylated peptides, said method comprising:
   (a) contacting said mixture with ceramic hydroxyapatite in an alkaline binding buffer solution to cause phosphorylated peptides in said mixture to bind to said ceramic hydroxyapatite preferentially relative to said non-phosphorylated peptides, and
   (b) eluting phosphorylated peptides so bound from said ceramic hydroxyapatite with an alkaline elution buffer, in an eluate as said product solution.

2. The method of claim 1 wherein said ceramic hydroxyapatite is a calcium-pretreated hydroxyapatite by incubation with a calcium chloride solution.

3. The method of claim 2 wherein said calcium chloride solution is an aqueous solution containing about 30 mM to about 300 mM calcium chloride at approximately neutral pH.

4. The method of claim 1 wherein said (b) comprises eluting said phosphorylated peptides with an elution buffer comprising potassium phosphate monobasic at a pH of about 9.0 to about 11.0.

5. The method of claim 1 wherein said (b) comprises eluting said phosphorylated peptides with an elution buffer comprising potassium phosphate monobasic at a pH of about 9.5 to about 10.5.

6. The method of claim 1 wherein:
   said mixture contains a plurality of phosphorylated peptides comprising mono-phosphorylated peptides and multi-phosphorylated peptides,
   the residue of said mixture passing through said ceramic hydroxyapatite in step (a) is defined as a flow-through fraction, and
   step (b) is performed in a plurality of stages comprising (i) a first stage in which elution is performed with a low-stringency alkaline buffer to produce a first eluate and (ii) a second stage, subsequent to said first stage, in which elution is performed with a high-stringency alkaline buffer to produce a second eluate, said first eluate being enriched in mono-phosphorylated peptides relative to said flow-through fraction and said second eluate, and said second eluate being enriched in multi-phosphorylated peptides relative to said flow-through fraction and said first eluate.

7. The method of claim 6 wherein said low-stringency alkaline buffer has a pH of about 8.5 to about 9.5, and said high-stringency alkaline buffer has a pH that exceeds the pH of said low-stringency buffer by a differential of 0.5 to 2.0.

8. The method of claim 4 wherein said alkaline binding buffer comprises acetonitrile and sodium bicarbonate at a pH of from about 8.0 to about 9.0, said low stringency alkaline buffer comprises acetonitrile, tris-(hydroxymethyl)¬aminomethane, and sodium phosphate monobasic at a pH of about 8.5 to about 9.5, and said high-stringency alkaline buffer comprises potassium phosphate monobasic at a pH that exceeds the pH of said low-stringency buffer by a differential of 0.5 to 2.0.

9. The method of claim 6 wherein said alkaline binding buffer comprises acetonitrile and sodium bicarbonate at a pH of from about 8.5, said low stringency alkaline buffer comprises acetonitrile, tris-(hydroxymethyl)¬aminomethane, and sodium phosphate monobasic at a pH of about 9.0, and said high-stringency alkaline buffer comprises potassium phosphate monobasic at a pH of about 10.0.

10. The method of claim 6 wherein
    said ceramic hydroxyapatite is pretreated by incubation with an aqueous solution containing about 30 mM to about 300 mM calcium chloride at approximately neutral pH, and
    said alkaline binding buffer comprises acetonitrile and sodium bicarbonate at a pH of from about 8.5, said low stringency alkaline buffer comprises acetonitrile, tris-hydroxymethyl)¬aminomethane, and sodium phosphate monobasic at a pH of about 9.0, and said high-stringency alkaline buffer comprises potassium phosphate monobasic at a pH of about 10.0.

11. The method of claim 1 wherein said phosphorylated peptides each contain a maximum of thirty amino acids.

\* \* \* \* \*